United States Patent [19]

Applegate

[11] 4,287,884
[45] * Sep. 8, 1981

[54] KNEE BRACE WITH SELECTIVELY VARIABLY POSITIONABLE PADS

[75] Inventor: Leslie T. Applegate, Cincinnati, Ohio

[73] Assignee: Surgical Appliance Industries, Inc., Cincinnati, Ohio

[*] Notice: The portion of the term of this patent subsequent to May 6, 1997, has been disclaimed.

[21] Appl. No.: 100,842

[22] Filed: Dec. 6, 1979

[51] Int. Cl.³ .............................................. A61F 3/00
[52] U.S. Cl. ......................... 128/80 C; 128/DIG. 15; 2/24
[58] Field of Search ................. 128/80 C, 87 R, 80 R, 128/165, DIG. 15; 2/22, 24

[56] References Cited

U.S. PATENT DOCUMENTS

| 2,188,718 | 1/1940 | Jung | 2/24 |
| 2,524,326 | 10/1950 | Murphy | 128/24 R |
| 3,046,981 | 7/1962 | Biggs, Jr. et al. | 128/80 C |
| 4,099,269 | 7/1978 | Porner | 2/22 |
| 4,116,236 | 9/1978 | Albert | 128/80 C |
| 4,201,203 | 5/1980 | Applegate | 2/24 |

Primary Examiner—Robert W. Michell
Assistant Examiner—Arthur S. Rose
Attorney, Agent, or Firm—Wood, Herron & Evans

[57] ABSTRACT

A knee brace including an elastic sleeve stretchable in a circumferential direction, a plurality of individual pad mounts permanently fixed to the interior of the sleeve which are disposed in a generally circular array to surround a substantial portion of the wearer's patella, and at least one resilient pad selectively removably engageable with different of said individual pad mounts for selectively removably mounting the pad at different positions relative to the wearer's patella to provide patella support at selectively variable positions as dictated by the individual needs of the wearer.

2 Claims, 4 Drawing Figures

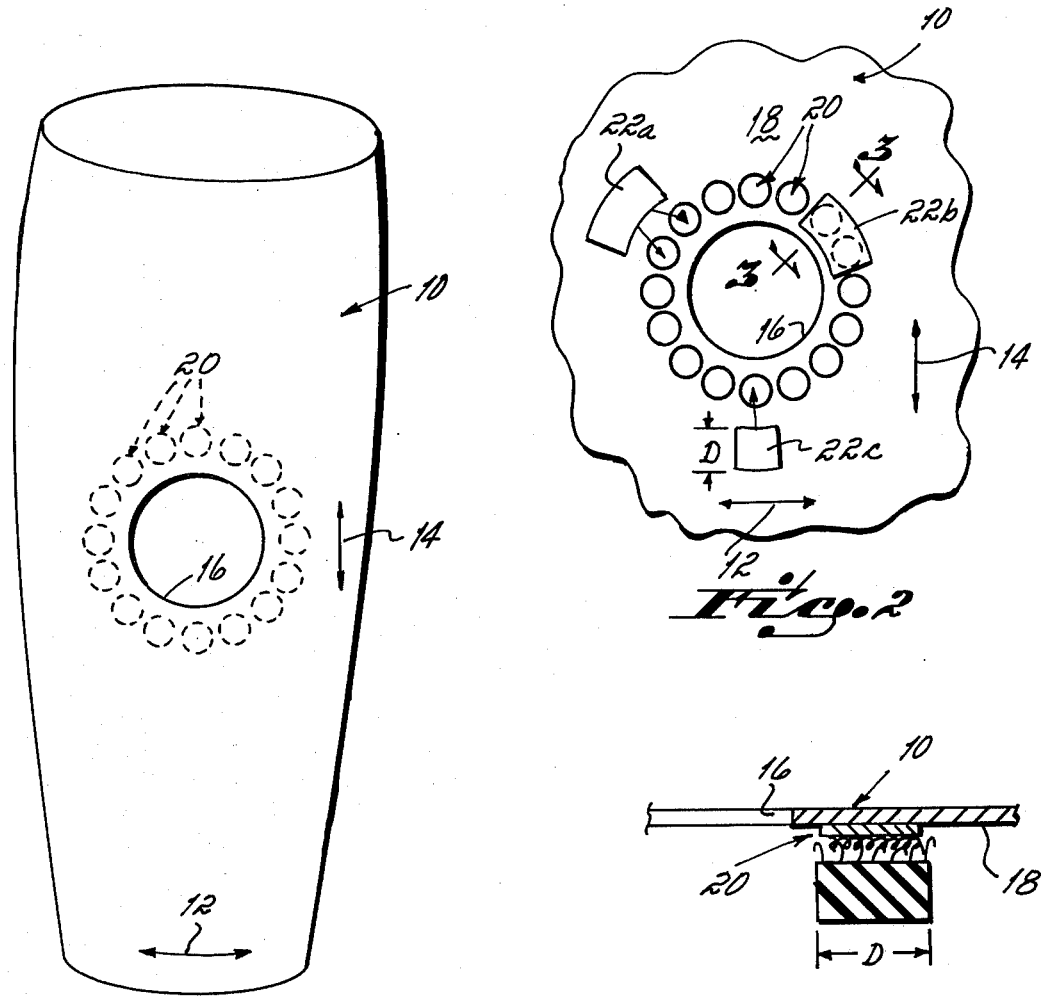
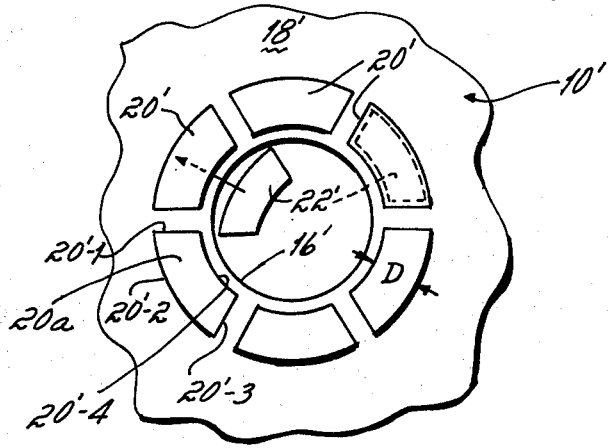

KNEE BRACE WITH SELECTIVELY VARIABLY POSITIONABLE PADS

This invention relates to elastic knee braces of the type having internal pads for supporting and protecting the patella.

U.S. patent application Ser. No. 100,851 discloses and claims subject matter related to the invention disclosed and claimed in the present application.

For many years knee braces have been used of the type having an elastic sleeve for applying compressive forces to the knee and internal pads for supporting and protecting the patella. One of the shortcomings of knee braces of this type heretofore known is the difficulty, utilizing a knee brace of fixed dimensions and configuration, to properly fit it to the knees of persons having different knee shapes, sizes, configurations, etc. An elastic knee brace having patella supporting and protecting pads designed to fit a person having a particular size and shape patella will typically not properly fit another person having a differently sized and shaped patella. Since it is important to have the patella supporting and protecting pads snugly embrace the periphery of the wearer's patella, it is extremely desirable to have a knee brace which permits the pads to be arranged differently for different persons having varying patella sizes and shapes.

Accordingly, it has been an objective of this invention to provide a knee brace which, while standard in design and construction, snugly embraces the periphery of a user's patella regardless of variations in the size and/or shape of the patella. This objective has been accomplished in accordance with certain principles of this invention by securing to the interior of a tubular elastic sleeve a plurality of individual pad mounts which are disposed in a generally circular array surrounding a substantial portion of the wearer's patella, and providing at least one, and preferably several, resilient pads which are selectively removably engageable with different ones of said individual pad mounts for selectively removably mounting the pads at different positions relative to the wearer's patella. In this way, the configuration and location of the pads can be varied to snugly embrace differently sized and configured patellas to provide the necessary support and protection therefor as dictated by the individual needs of the wearer.

These and other advantages and objectives of the invention will become more readily apparent from the detailed description of the preferred embodiments thereof taken in conjunction with the drawings in which FIG. 1 is a perspective view of the front of one preferred form of the knee brace of this invention utilizing Velcro pad mounts to fasten the pads as desired;

FIG. 2 is an elevational view of the interior of the front section of the embodiment depicted in FIG. 1;

FIG. 3 is a cross-sectional view along line 3—3 of FIG. 2; and

FIG. 4 is an elevational view of the interior of another embodiment of the invention utilizing multiple pad-receiving pockets.

As shown in FIGS. 1-3, one form of the invention includes a tubular elastic sleeve 10 which is preferably stretchable in a circumferential direction as indicated by the double-headed arrow 12. If desired the sleeve 10 can also be stretchable in a longitudinal or vertical direction as indicated by the double-headed arrow 14. The length of the sleeve 10 measured in a vertical direction is sufficient to not only cover the user's kneecap, or patella, but also to extend 3-6 inches above and below the patella. The circumferential dimension, or girth, of the sleeve 10 is such that when the sleeve 10 is positioned about the knee it applies compressive forces to the wearer's knee in a radially inward direction. Preferably, the front central section of the sleeve 10 is provided with a patella opening 16 dimensioned and configured to snugly embrace the periphery of the user's patella when the sleeve is worn.

Surrounding the patella opening 16 and mounted to the internal surface 18 of the sleeve are a plurality of pad-mounting means 20 for mounting, at selectively variable positions around the patella opening 16, pad means indicated generally by the reference numeral 22. The pad means 22 may take the form of individual, physically discrete pads 22a and 22b. The mounting means 20 in a preferred form are Velcro patches having loops (or hooks) which cooperate with corresponding hooks (or loops) of Velcro patches secured to the back surfaces of the pad means 22. The array of mounting means surrounding the patella opening 16 permit the pad means to be mounted at different positions relative to the patella opening 16, such as above the opening, below the opening, on either side of the opening, etc. as well as permitting the pads to be mounted over a limited range of different distances from the patella opening 16, that is, closer or further from the opening as desired. In this way the composition, arrangement, and configuration of the pads may be varied to suit the individual needs of the wearer's own knee and patella.

In accordance with a further embodiment of the invention depicted in FIG. 4, the array of Velcro pad-mounting fasteners 20 is substituted by an array of pad-receiving pockets 20' for selectively receiving pad means 22 consisting of individual pads 22a and 22b. Each of the pockets 20' is formed by stitching to the interior of the sleeve a generally rectangular piece of material 20a along three edges thereof, such as edges 20'-1, 20'-2, and 20'-3. The pocket is defined by the rectangular piece of material 20a and the underlying portion of the sleeve. When the pocket is so stitched, the innermost edge 20'-4 is left unstitched to provide an opening in the pocket for insertion of a pad, such as pad 22b. This embodiment, like the embodiment of FIGS. 1-3, permits the number and location of pads used to be varied depending upon the peculiar needs of the user. While it may be desired in some cases to position a pad within each pocket 20', this is not necessary and will depend on the needs of the wearer.

In the embodiment shown in FIGS. 1-3, the pads may be sized to cooperate with one, two, . . . n individual mounting elements 20. In this way, a pad of unit size, such as pad 22c, mounts on a single mounting element 20, while a pad of double unit size, such as pad 22b, mounts on two of the individual mounts 20, 20.

With both embodiments described, the pad mounts are located, and the pads sized, relative to the patella such that the inner edges of the pads snugly embrace the periphery of the wearer's patella, thereby providing the support and protection desired. The radial dimension D of the pads is selected, as needed, to provide the desired degree of protection and support to the knee.

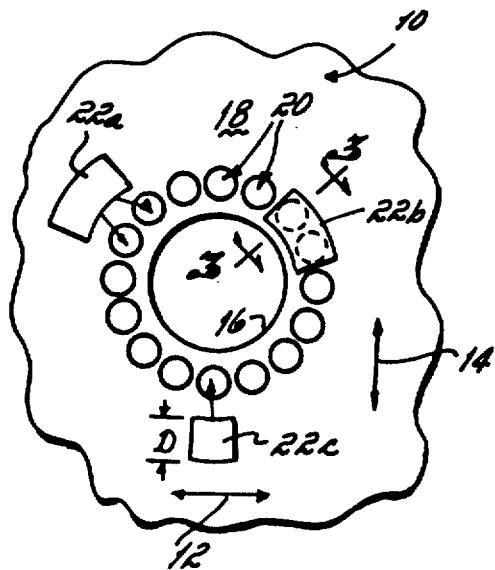

I claim:

1. An improved knee brace comprising:
   a tubular elastic sleeve dimensioned and configured to apply radially inwardly directed compressive forces to the wearer's knee when placed thereabout, at least four individual pad mounts of substantially identical size permanently fixed to the interior of said sleeve and disposed in a generally circular array surrounding a substantial portion of the wearer's patella, including portions above, below, and on either side of the patella, said mounts being free of direct interconnection therebetween to enable said elastic sleeve to stretch to enlarge the diameter of said circular array when placed on knees of varying girth, at least a first resilient pad of unit size and at least a second resilient pad of N-unit size where N is an integer larger than one, said pads each selectively removably engageable with different individual pad mounts for selectively removably mounting said pads at different positions relative to the wearer's patella to provide support and protection for the wearer's patella at variable locations thereof as dictated by the individual needs of the wearer, the ratio between the number of pad mounts engaged by said second and first pads being N.

2. The knee brace of claim 1 wherein said pad mounts and pads each include cooperating Velcro fastening means.

* * * * *

UNITED STATES PATENT AND TRADEMARK OFFICE
CERTIFICATE OF CORRECTION

PATENT NO. : 4,287,884

DATED : September 8, 1981

INVENTOR(S) : Leslie T. Applegate

It is certified that error appears in the above—identified patent and that said Letters Patent is hereby corrected as shown below:

The Title page showing the illustrative figure of drawing should appear as per attached sheet.

Signed and Sealed this

Ninth Day of March 1982

[SEAL]

Attest:

GERALD J. MOSSINGHOFF

Attesting Officer    Commissioner of Patents and Trademarks

United States Patent [19]

Applegate

[11] 4,287,884
[45] * Sep. 8, 1981

[54] KNEE BRACE WITH SELECTIVELY VARIABLY POSITIONABLE PADS

[75] Inventor: Leslie T. Applegate, Cincinnati, Ohio

[73] Assignee: Surgical Appliance Industries, Inc., Cincinnati, Ohio

[ * ] Notice: The portion of the term of this patent subsequent to May 6, 1997, has been disclaimed.

[21] Appl. No.: 100,842

[22] Filed: Dec. 6, 1979

[51] Int. Cl.³ .............................................. A61F 3/00
[52] U.S. Cl. ........................ 128/80 C; 128/DIG. 15; 2/24
[58] Field of Search ............... 128/80 C, 87 R, 80 R, 128/165, DIG. 15; 2/22, 24

[56] References Cited

U.S. PATENT DOCUMENTS

| | | | |
|---|---|---|---|
| 2,188,718 | 1/1940 | Jung | 2/24 |
| 2,524,326 | 10/1950 | Murphy | 128/24 R |
| 3,046,981 | 7/1962 | Biggs, Jr. et al. | 128/80 C |
| 4,099,269 | 7/1978 | Porner | 2/22 |
| 4,116,236 | 9/1978 | Albert | 128/80 C |
| 4,201,203 | 5/1980 | Applegate | 2/24 |

Primary Examiner—Robert W. Michell
Assistant Examiner—Arthur S. Rose
Attorney, Agent, or Firm—Wood, Herron & Evans

[57] ABSTRACT

A knee brace including an elastic sleeve stretchable in a circumferential direction, a plurality of individual pad mounts permanently fixed to the interior of the sleeve which are disposed in a generally circular array to surround a substantial portion of the wearer's patella, and at least one resilient pad selectively removably engageable with different of said individual pad mounts for selectively removably mounting the pad at different positions relative to the wearer's patella to provide patella support at selectively variable positions as dictated by the individual needs of the wearer.

2 Claims, 4 Drawing Figures